(12) United States Patent
Tsuchiya et al.

(10) Patent No.: US 6,500,201 B1
(45) Date of Patent: Dec. 31, 2002

(54) HEATER

(75) Inventors: Masaru Tsuchiya, Tokyo (JP); Takashi Ito, Tokyo (JP); Akira Shiga, Tokyo (JP); Takao Orii, Tokyo (JP); Hiroaki Kobayashi, Tochigi (JP); Masamichi Shigekane, Tokyo (JP); Akira Noda, Tochigi (JP); Koji Mimura, Tochigi (JP)

(73) Assignee: Kao Corporation, Tokyo (JP)

( * ) Notice: Subject to any disclaimer, the term of this patent is extended or adjusted under 35 U.S.C. 154(b) by 0 days.

(21) Appl. No.: 09/762,702

(22) PCT Filed: Aug. 9, 1999

(86) PCT No.: PCT/JP99/04303

§ 371 (c)(1),
(2), (4) Date: Mar. 19, 2001

(87) PCT Pub. No.: WO00/08968

PCT Pub. Date: Feb. 24, 2000

(30) Foreign Application Priority Data

Aug. 11, 1998 (JP) .......................................... 10/226795

(51) Int. Cl.$^7$ .................................................. A42B 1/00
(52) U.S. Cl. .................................................. 607/110
(58) Field of Search ................................ 607/110, 108, 607/109, 111

(56) References Cited

U.S. PATENT DOCUMENTS

| | | | | |
|---|---|---|---|---|
| 3,463,161 A | * | 8/1969 | Andrassy | 607/110 |
| 4,061,898 A | * | 12/1977 | Murray et al. | 607/110 |
| 4,356,709 A | * | 11/1982 | Alexander | 607/110 |
| 4,382,446 A | * | 5/1983 | Truelock | 607/110 |
| 5,129,391 A | * | 7/1992 | Brodsky et al. | 607/110 |
| 5,480,418 A | | 1/1996 | Zeoli-Jones | 607/110 |
| 5,837,005 A | * | 11/1998 | Viltro et al. | 607/110 |
| 5,850,636 A | * | 12/1998 | Reuuen | 607/110 |
| 5,950,234 A | * | 9/1999 | Leong et al. | 607/110 |

FOREIGN PATENT DOCUMENTS

| | | |
|---|---|---|
| JP | 62-23602 | 2/1987 |
| JP | 62-295608 | 12/1987 |
| JP | 5-91505 | 12/1993 |
| JP | 10-108719 | 4/1998 |

* cited by examiner

*Primary Examiner*—Paul J. Hirsch
(74) *Attorney, Agent, or Firm*—Oblon, Spivak, McClelland, Maier & Neustadt, P.C.

(57) ABSTRACT

A heater comprises a cap 20 formed by joining and fixing together curved peripheries 10a as peripheries of two semi-elliptical heat-generator-containing sheets 10 of generally the same shape. The heat-generator-containing sheet 10 comprises a waterproof inner layer sheet 2, an air-permeable sheet 5 disposed so as to cover the entire surface of the inner layer sheet 2, and a plurality of heat generators 3 interposed between and held by the inner layer sheet 2 and the air-permeable sheet 5, which generate heat when in contact with an air. The heat generators 3 are disposed substantially over the entire surface of the cap 20. The heat-generator-containing sheets 10 are joined and fixed together with the respective inner layer sheets 2 being the inner surface. The heater realizes a simple handling when in use, a small temperature variation, and simple fabrication process.

7 Claims, 7 Drawing Sheets

HEATER

TECHNICAL FIELD

The present invention relates to a heater which easily heats one's hair or scalp and which is suitable for use in hair treatments such as hair curling or waving, treatment, hair softening, the straightening of curled hair, resilience rendering, the improvement of a hair condition, and a coloring; and hair treatments such as hair growing and fostering treatments, and a scalp care, and a method for fabricating the same.

BACKGROUND ART

A hair cap which is used for performing hair curling or waving at home with ease has been proposed as a hair heater. As a heat source thereof, an iron powder pocket warmer, a heat reservoir such as paraffin or polyethylene glycol, a heat generator which generates heat by the flow of electricity, for example, to a nichrome wire, or the like, has been proposed. In particular, the iron powder pocket warmer is superior to others in terms of its convenience, safety, durability, etc. Therefore, a variety of hair heaters which use iron powder pocket warmers have been proposed.

Japanese Patent Laid-Open Publication No. 10-108719 discloses a cap for heating the hair and scalp, which is used by inserting commercially available pocket warmers into pockets provided along an inner surface or outer surface of a cap member. However, the cap has such problems that the handling of the cap when in use is complicated; it is impossible to completely cover a head with a plurality of commercially available quadrilateral-shaped pocket warmers; and a temperature variation is likely to occur in the hair because the pocket warmers are insufficiently fitted to the hair.

Japanese Utility Model Laid-Open Publication No. 62-23602 discloses a heating cap comprising an inner skin, an outer skin, and a heat generating powder filled therebetween. However, the cap has a structure such that the heat generating powder is difficult to be divided into portions. As a result, it is difficult to fill the heat generating powder uniformly, so that a temperature variation is likely to be caused. Also, there was a problem such that the cap cannot be folded.

Moreover, the iron powder pocket warmer has a characteristic such that it generates heat when exposed to an air containing oxygen. Therefore, especially when a cap which employs a pocket warmer as a heat generator is fabricated, an additional time is required to incorporate the pocket warmer into the cap, as compared to the case where a sheet-like pocket warmer is fabricated. Thus, the problems of the heat generation and the deactivation of the pocket warmer powder due to the heat generation become more acute. Therefore, the fabrication of a heater which employs an iron powder pocket warmer as a heat generator needs to be simple.

DISCLOSURE OF THE INVENTION

Therefore, an object of the present invention is to provide a heater which is easy to handle when in use, which has a small temperature variation, and which is easy to fabricate.

The present invention is to provide a heater, comprising a cap having a heating section,
wherein said heating section comprises a waterproof inner layer sheet, an air-permeable sheet disposed so as to cover said inner layer sheet, and a plurality of heat generators which are interposed between and held by said inner layer sheet and said air-permeable sheet and which generate heat when in contact with an air, and
said heat generators are arranged substantially over an entire surface of the cap.

By providing such a heater, the above-described object is achieved.

The heater of the present invention can minimize the loss of iron powder due to the heat generation during the fabrication thereof; is easy to handle when in use; has a small temperature variation; and is easy to fabricate.

DETAILED DESCRIPTION OF THE INVENTION

A heater according to a preferred embodiment of the present invention will be described below.

Figure 1:
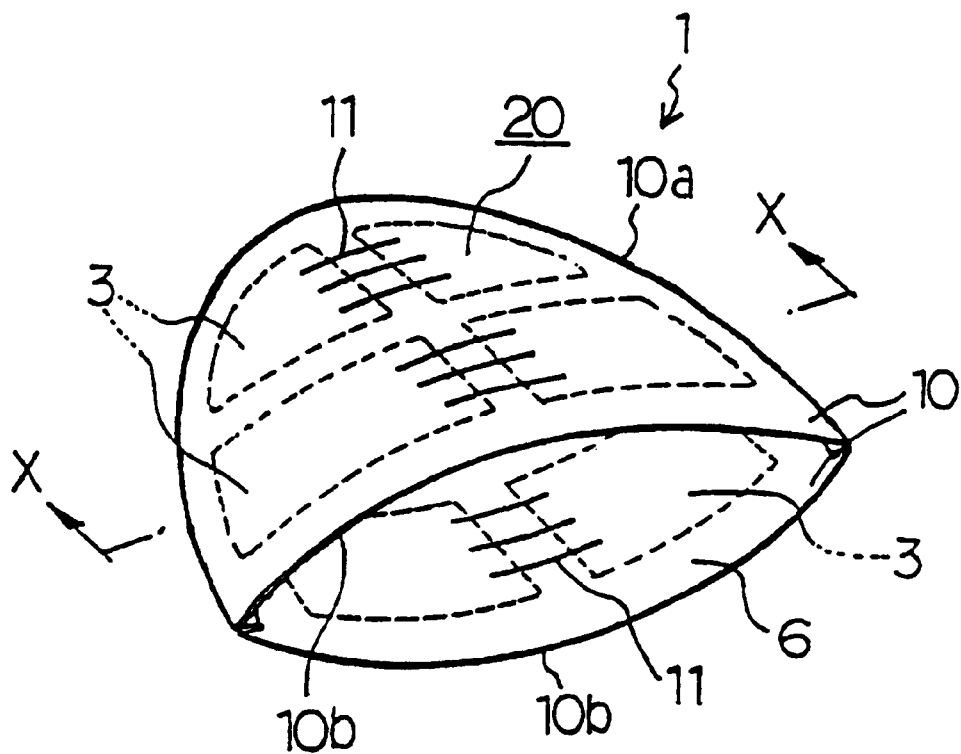
FIG. 1 is a perspective view showing a preferred embodiment of a heater according to the present invention.
Figure 2:
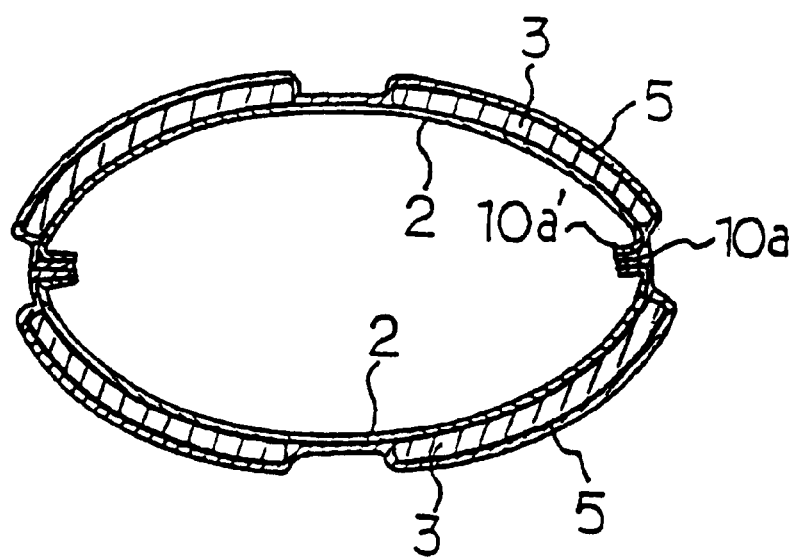
FIG. 2 is a cross-sectional view of the heater shown in FIG. 1 taken along a line X—X.

A heater 1 according to the present embodiment (the first embodiment) shown in FIGS. 1 and 2 comprises a cap having a heating section.

In the present embodiment, there is provided a cap 20 formed by joining and fixing together curved peripheries 10a as respective peripheries of two semi-elliptical heat-generator-containing sheets 10 of generally the same shape. The heat-generator-containing sheet 10 comprises a waterproof inner layer sheet 2, an air-permeable sheet 5 provided so as to cover the entire surface of the inner layer sheet 2, and a plurality of heat generators 3 which are interposed between and fixed by the inner layer sheet 2 and the air-permeable sheet 5 and which generate heat when in contact with an air. The heat generators 3 are disposed substantially over the entire surface of the cap 20, thereby forming a heating section. The heat-generator-containing sheets 10 are joined and fixed together so that the inner layer sheets 2 become inner surfaces of the cap.

Herein, the aforementioned phrase "disposing substantially over the entire surface of the cap 20" means that the heat generators are disposed so as to be able to heat an object to be heated entirely when in use.

More specifically, the heater 1 of the present embodiment is comprised solely of the cap 20. Moreover, the air-permeable sheets 5 are made contact with each other and the curved peripheries 10a are then heat-sealed, thereby joining and fixing the curved peripheries 10a. The sealed portions 10a' are located at the side of the inner surface of the heater.

As shown in FIG. 1, in the heater 1 of the present embodiment, string-shaped elastic members 11 are adhered to the inner layer sheets 2 and disposed at the sides of the respective heat generators 3 so as to make connections between the respective heat generators 3. Gathers are formed between the plurality of heat generators 3 disposed in the width direction of the heater 1. In other words, the inner layer sheet 2 is a sheet on which the elastic members are disposed.

The respective heat generators 3 are separated from one another by respectively joining the inner layer sheets 2 and the air-permeable sheets 5 together.

As the inner layer sheet 2, a raw material having water resistance and flexibility, e.g., a polyethylene sheet, a polypropylene sheet, a vinyl chloride sheet, etc., is used.

In addition to an air-permeable sheet used, for example, in a general disposable pocket warmer, any air-permeable sheet can be used as the air-permeable sheet 5 without any particular limitations.

As in the general disposable pocket warmer, the above-described heat generator 3 is formed by a heat generator composition whose main component is iron powder. Incidentally the heat generator may be used by enclosing it in an inner bag (not shown), or the like.

As the elastic member, a rubber material, e.g., polyurethane rubber, a cross-linked natural rubber, an elastic tape used for a diaper, a stretchable nonwoven fabric, etc., is used.

In the first embodiment, the elastic members 11 may be adhered to the air-permeable sheets 5. Therefore, the air-permeable sheets 5 can be used as sheets on which the elastic members are disposed. Alternatively, without using the elastic members 11, either the above-described inner layer sheet 2 or the above-described air-permeable sheet 5 may be formed by a sheet having an elasticity so that gathers are formed between the heat generators. The shape of the heat-generator-containing sheet may be, for example, a quadrilateral such as a rectangle, instead of a semi-ellipse.

In order to enhance the thermal conductivity and to avoid a temperature variation in the hair, thin metal sheets (such as aluminum foils) can be attached between the heat generators.

A heat generation temperature and a heat generation time of the heater of the present embodiment can be suitably adjusted by the permeability of the outer layer sheet and the composition of the heat generator composition. Especially when the heater is used for heating one's hair and scalp, it is preferred to make an adjustment to produce the temperature characteristics such that the temperature is raised to 35 to 40° C. within ten minutes and a temperature of 40 to 60° C. is lasted for 10 to 120 minutes in the case where the heater is put on the wet hair soaked with water, or the like, in a room at 25° C.

The heater of the present embodiment is preferably used for heating the hair and scalp, and it can be also used for keeping foodstuffs warm. When used for heating the hair and scalp, a sealed package is opened to take out the heater from the package as will be described below, and the heater is used, for example, by putting it on the head through the opening thereof.

The heater of the present embodiment can be used with a simple handling, and can safely heat the hair and scalp. Moreover, since the heater of the present embodiment can be fabricated as will be described below, the loss of iron powder is small, thereby being able to achieve the efficient fabrication.

Next, a preferred method for fabricating the heater of the present embodiment will be described.

The heater of the present embodiment can be fabricated by performing a heat-generator-containing sheet producing step of producing the heat-generator-containing sheet in which the inner layer sheet and the air-permeable sheet are attached together with the heat generators being enclosed therebetween at predetermined positions; an overlaying step of folding the obtained heat-generator-containing sheet into two with the air-permeable sheet side being the inner side, or overlaying the obtained two heat-generator-containing sheets on each other with the air-permeable sheet side being the inner side; and a sealing step of sealing the peripheries overlaid on each other so as to isolate the heat generators from the ambient air.

The above-described fabrication method can adopt two methods, i.e., the case where the heat-generator-containing sheet has the shape of an ellipse (such a case is referred to as a "fabrication method A"), and the case where the heat-generator-containing sheet has the shape of a semi-ellipse (such a case is referred to as a "fabrication method B").

The both methods will be described below separately.

<As to Fabrication Method A>

Figure 3:
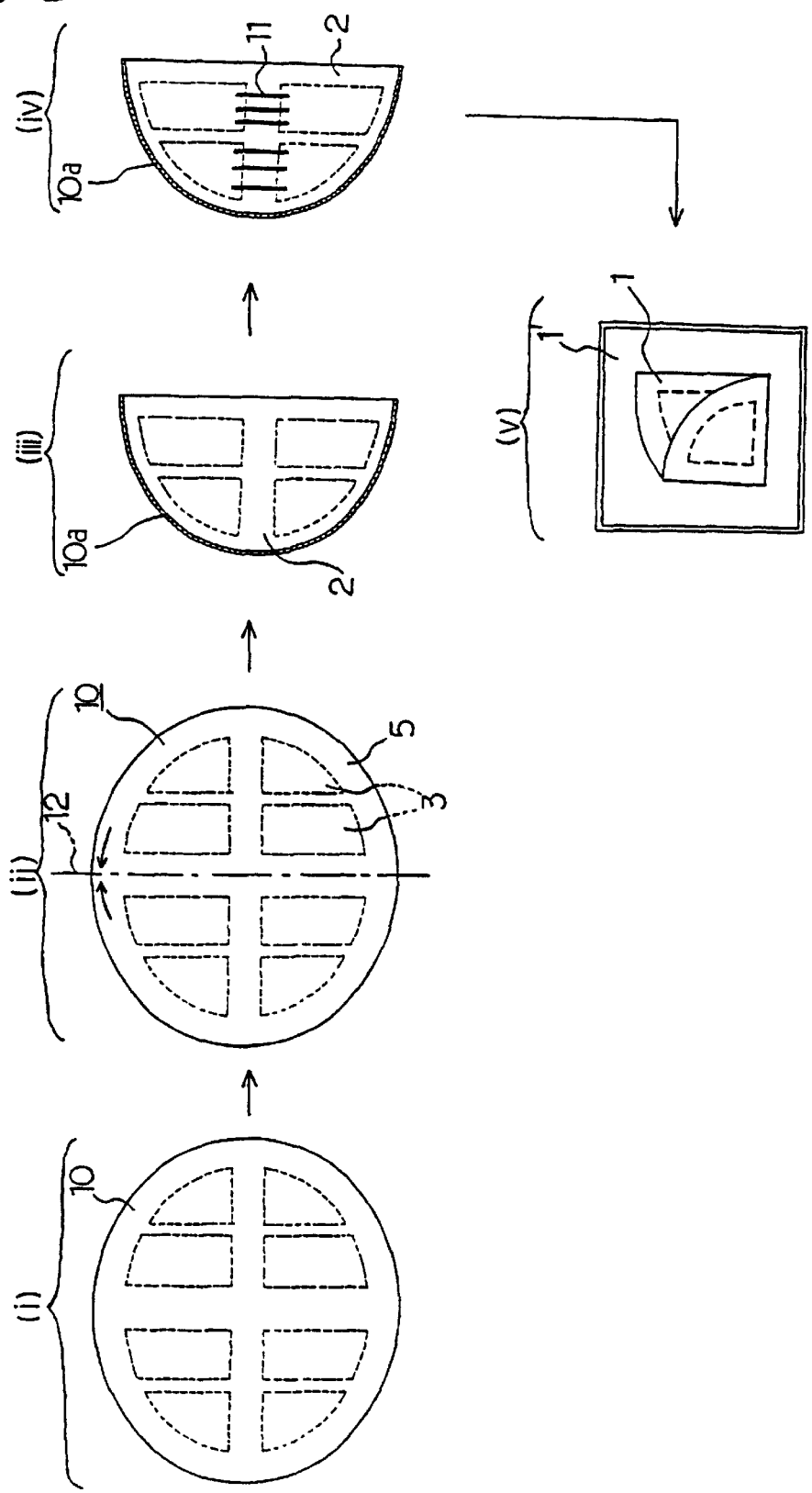
FIG. 3 is a process diagram illustrating an essential part of a method for fabricating the heater shown in FIG. 1.

First, as shown in FIG. 3, the heat-generator-containing sheet 10 of an elliptical shape is produced in the heat-generator-containing sheet producing step (i). As in a method for fabricating a general disposable pocket warmer using iron powder, the heat-generator-containing sheet producing step (i) can be performed as follows. An raw fabric sheet of the inner layer sheet and an raw fabric sheet of the air-permeable sheet are attached together with a heat generator composition being enclosed in predetermined positions so as to produce a continuous sheet such that the inner layer sheet and the air-permeable sheet are attached together with the heat generators being formed therebetween, and the continuous sheet is, for example, cut into a desired elliptical shape (not shown). As a result, the heat-generator-containing sheet 10 of an elliptical shape as shown in FIG. 3 can be obtained. Incidentally the raw fabric sheet itself may have an elliptical shape.

Next, as shown in FIG. 3, the overlaying step (ii) is performed by folding the heat-generator-containing sheet in arrow directions at a folding line positioned at an approximate center of the heat-generator-containing sheet in the longitudinal direction thereof so that the portions of the air-permeable sheet 5 are in contact with each other.

Furthermore, as shown in FIG. 3, the sealing step (iii) is performed by joining and fixing together curved peripheries of the two heat-generator-containing sheets overlaid on each other. The "joining and fixing" is not particularly limited thereto as long as the ambient air cannot enter the side of the heat generators 3 by employing heat sealing, an adhesive, or the like. In the present embodiment, the joining and fixing is performed by heat sealing.

As shown in FIG. 3, the heater 1 (a packaged product 1' of the heater 1) of the present embodiment can be obtained by performing, depending on the necessity, an elastic member attaching step (iv) of attaching the elastic members 11 at predetermined positions on the inner layer sheet 2 which is the outer surface of the heat-generator-containing sheet 10 whose periphery is sealed; a packaging step (v) of cutting the sealed heat-generator-containing sheet along a linear periphery thereof and unsealing the sealed heat-generator-containing sheet so as to form a cap with a circular opening (not shown), reversing the obtained cap so that the air-permeable sheet becomes the outer surface thereof (not shown), folding the cap by heat generators, sealing the cap with an air-impermeable sheet made of an oxygen-impermeable material such as polyvinylidene chloride, polyamide, polyester, etc., while performing degassing, and the like.

Without performing the packaging step, the heat-generator-containing sheet 10 whose periphery is sealed can be provided to a user as it is. In such a case, upon its use, the user cuts the heat-generator-containing sheet along a predetermined cutting line and unseals it so as to form an opening.

<As to Fabrication Method B>

In the following description, the same points as those in the fabrication method A will be omitted, and points different from those of the fabrication method A will be specifically described. Regarding points which will not be specifically described, the description in the description of the fabrication method A will be suitably applied thereto.

Figure 4:
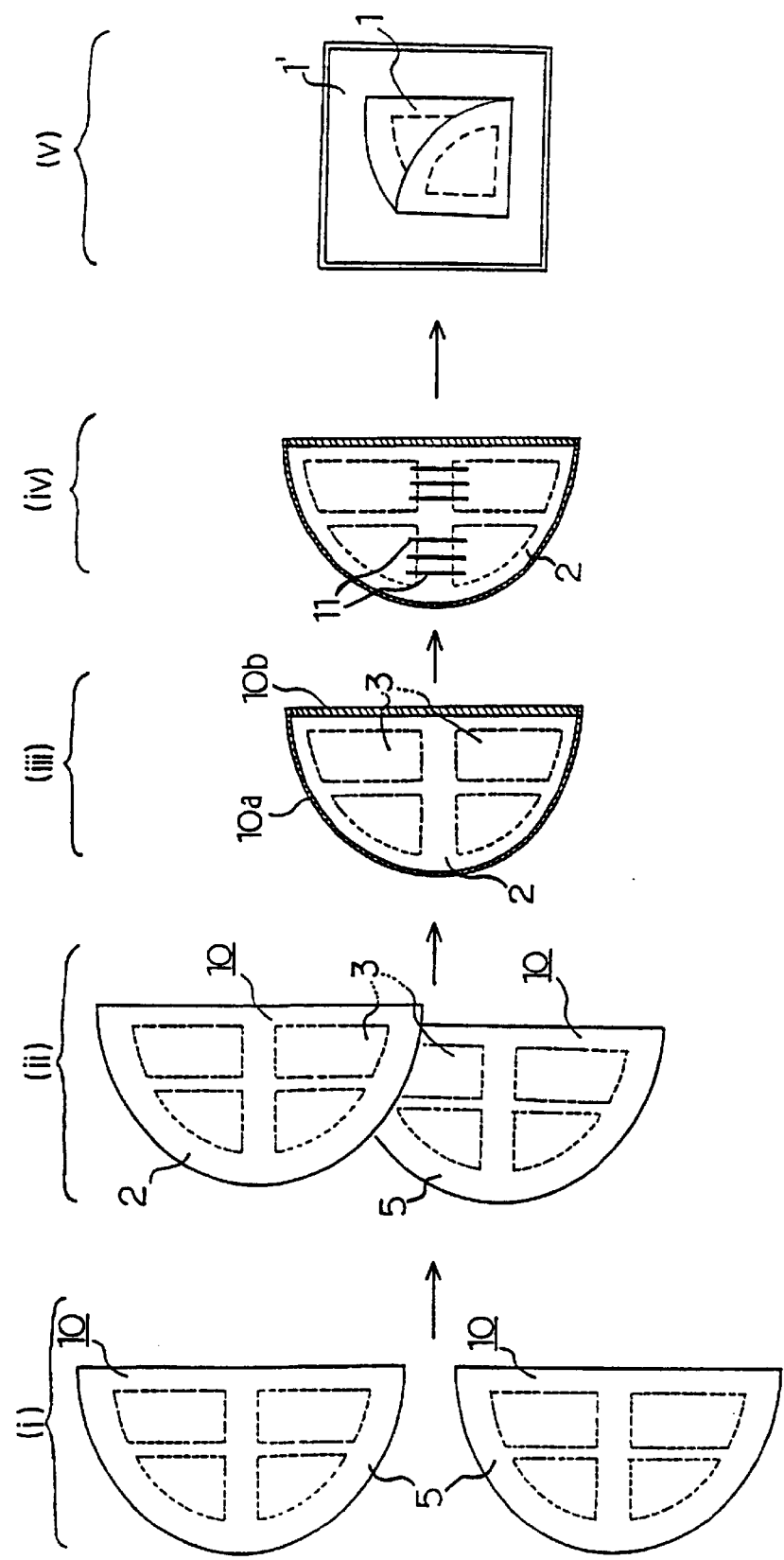
FIG. 4 is a process diagram illustrating an essential part of another method for fabricating the heater shown in FIG. 1.

In this method, first, two heat-generator-containing sheets 10 each having a semi-elliptical shape are produced in the heat-generator-containing sheet producing step (i), as shown in FIG. 4. Except for this point, the heat-generator-containing sheet producing step (i) can be performed in the same manner as that of the fabrication method A.

Next, as shown in FIG. 4, the overlaying step (ii) is performed by overlaying the two heat-generator-containing sheets 10 on each other so that the air-permeable sheets 5 thereof are in contact with each other. The sealing step (iii) is performed by joining and fixing together the curved and linear peripheries 10*a* and 10*b* respectively overlaid on each other.

As shown in FIG. 4, the heater (the packaged product of the heater) of the present embodiment can be obtained by performing, depending on the necessity, an elastic member attaching step (iv), a packaging step (v), and the like.

According to the fabrication method of the present embodiment, the attaching of the elastic members, or the like, can be performed with the heat generators being isolated from the ambient air, reducing the loss in the heat generators. Therefore, the method is excellent in the operability, and thus in the productivity.

Next, a heater according to the preferred second embodiment of the present invention will be described.

Points different from those of the above-described first embodiment will be specifically described, and the same points as those in the first embodiment will be omitted. Regarding points which will not be specifically described, the description made in the description of the first embodiment will be suitably applied thereto.

Figure 5:
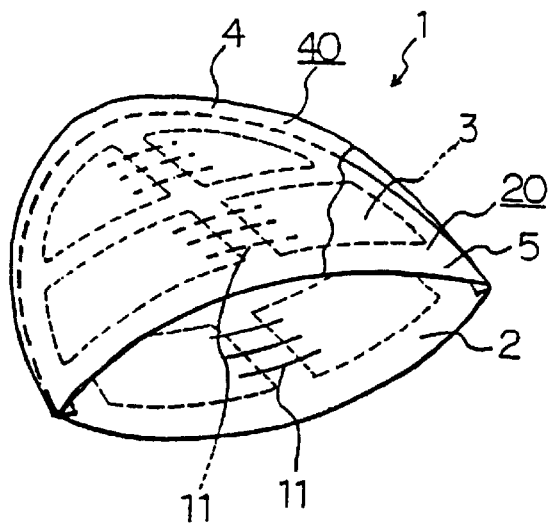
FIG. 5 is a perspective view showing the second embodiment of a heater according to the present invention.

As shown in FIG. 5, a heater 1 of the second embodiment is obtained by providing an outer layer cap 40 comprising an air-permeable and water-impermeable outer layer sheet 4 on the outer surface of the air-permeable sheet 5 of the cap 20 in the heater shown in FIG. 1, and by fixing the cap 20 and the outer layer cap 40 at the side of the respective openings. In other words, in the present embodiment, the outer layer cap 40 is further added to the heater of the embodiment shown in FIGS. 1 and 2.

The outer layer sheet 4 is an air-permeable and water-impermeable sheet which produces a water resistance and a heat retaining property. For example, an air-permeable/water-impermeable sheet, for example, used for a disposable diaper, or the like, may be used.

In this case, the air-permeable and water-impermeable sheet forming the outer layer sheet is preferably a moisture-permeable sheet. The moisture-permeable sheet is preferably water-impermeable, and has a moisture permeability larger than that of the air-permeable sheet. More specifically, the moisture permeability thereof is preferably 400 g/m$^2$·day or more, and more preferably 1000 g/m$^2$·day or more.

The above-described moisture permeability is measured under the condition such that the temperature is 25° C. and the humidity is 90% in accordance with the method of JIS Z 0208.

Specific examples of a moisture-permeable sheet satisfying the above-described moisture permeability include a moisture-permeable and water-impermeable polyethylene sheet or the like which is generally used for a disposable diaper.

Since the heater 1 of the present embodiment comprises the water-impermeable outer layer cap 40, the heater can be used in a place where the heater may take water, e.g., in a bath. The air-permeable sheet 5 needs to be made air-permeable to a degree sufficient to allow the heat generators 3 to generate heat satisfactorily, and thus the air-permeable sheet 5 cannot be made water-impermeable. Therefore, in order for the heater to be usable in a bath, or the like, the structure of the present embodiment is preferred.

The heater of the present embodiment can be fabricated by fabrication methods C and D described below.

<Fabrication Method C>

A fabrication method comprises:

a heat-generator-containing sheet producing step of producing a heat-generator-containing sheet of an elliptical or semi-elliptical shape in which the inner layer sheet and the air-permeable sheet are attached together with the heat generators being enclosed therebetween at predetermined positions;

an outer layer sheet fixing step of fixing the outer layer sheet having approximately the same shape as that of the air-permeable sheet onto the air-permeable sheet in the above-described heat-generator-containing sheet;

an overlaying step of folding the obtained heat-generator-containing sheet of an elliptical shape into two with the air-permeable sheet side being the inner side, or overlaying the obtained two heat-generator-containing sheets each having a semi-elliptical shape on each other with the air-permeable sheet side being the inner side; and a sealing step of sealing the peripheries overlaid on each other so as to isolate the heat generators from the ambient air.

<Fabrication Method D>

A fabrication method comprises:

a heat-generator-containing sheet producing step of producing a heat-generator-containing sheet of an elliptical or semi-elliptical shape in which the inner layer sheet and the air-permeable sheet are attached together with the heat generators being enclosed therebetween at predetermined positions;

an overlaying step of folding the obtained heat-generator-containing sheet of an elliptical shape into two with the air-permeable sheet side being the inner side, or overlaying the obtained two heat-generator-containing sheets each having a semi-elliptical shape on each other with the air-permeable sheet being at the inner side;

a sealing step of sealing the peripheries overlaid on each other so as to isolate the heat generators from the ambient air; and an outer layer cap fixing step of cutting the sealed heat-generator-containing sheet along a linear periphery thereof and unsealing the sealed heat-generator-containing sheet so as to form a cap with a circular opening, reversing the obtained cap so that the air-permeable sheet becomes the outer surface thereof, putting an outer layer cap which is separately produced over the air-permeable sheet, and fixing predetermined positions of the outer layer cap and the cap.

Each of the fabrication methods will be described below in more detail.

Points different from those in the above-described fabrication methods A and B will be specifically described, and the same points as those in the above-described fabrication methods A and B will be omitted. Regarding points which will not be specifically described, the description made in the above-described fabrication methods A and B will be suitably applied thereto.

[As to Fabrication Method C]

The heat-generator-containing sheet producing step (i) is performed in the same manner as that of the fabrication method A.

Figure 6:
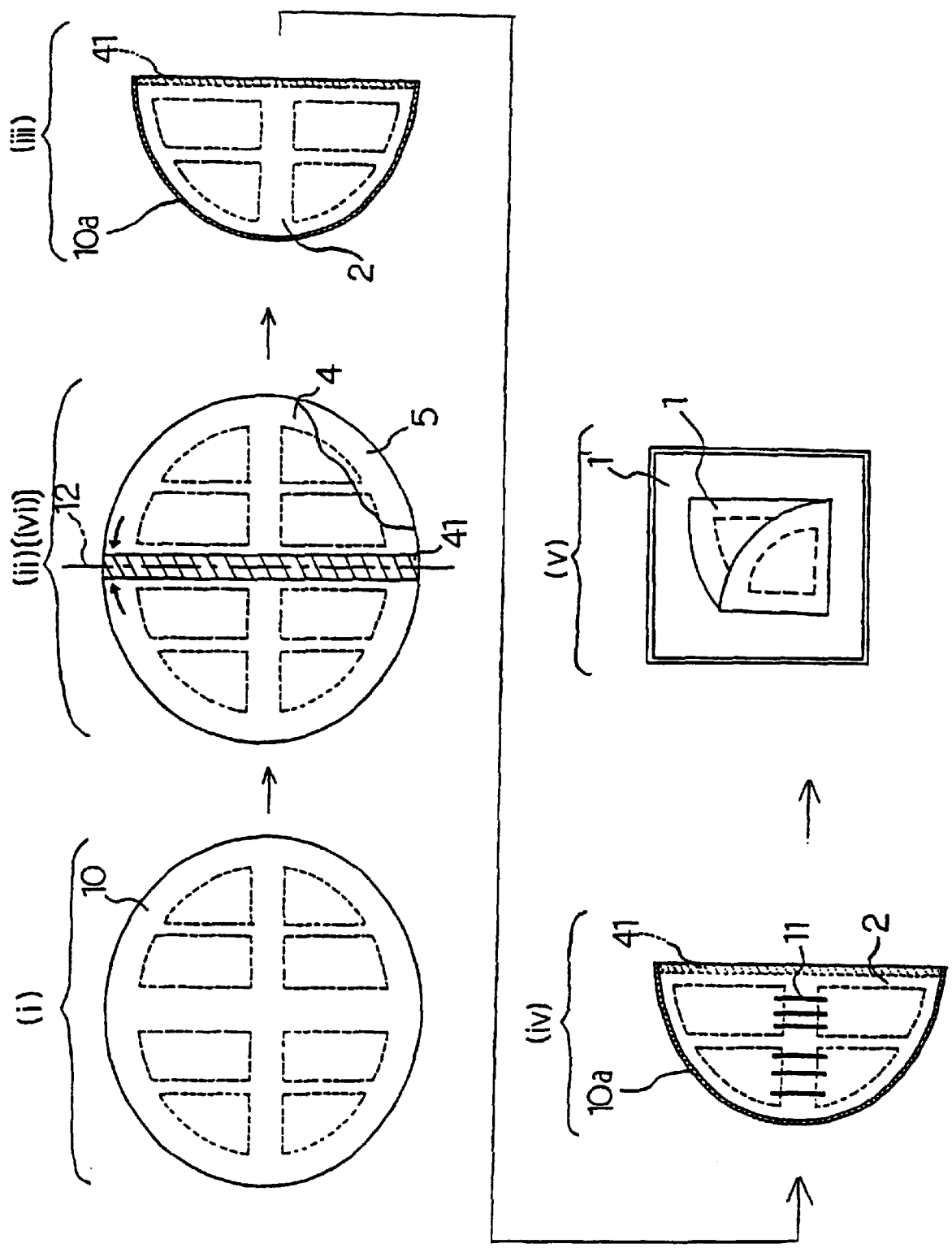
FIG. 6 is a process diagram illustrating an essential part of a method for fabricating the heater shown in FIG. 5.

As shown in FIG. 6, the outer layer sheet fixing step (vi) is performed by overlaying the outer layer sheet over the air-permeable sheet in the heat-generator-containing sheet of an elliptical shape which is obtained in the heat-generator-containing sheet producing step, and performing the joining and fixing of the outer layer sheet with a fixing portion 41 which is positioned at a center of the outer layer sheet in the longitudinal direction and has a predetermined width.

Next, the overlaying step (ii) is performed by folding the heat-generator-containing sheet 10 to which the outer layer sheet 4 is fixed, in the same manner as that of the overlaying step in the fabrication method A except that the outer layer sheet 4 is folded so that the portions thereof are in contact with each other. The sealing step (iii) is performed in the same manner as that of the fabrication method A.

Depending on the necessity, an elastic member attaching step (iv), a packaging step (v), and the like are further performed so as to obtain a heater (a packaged product of the heater) of the present embodiment.

Figure 7:
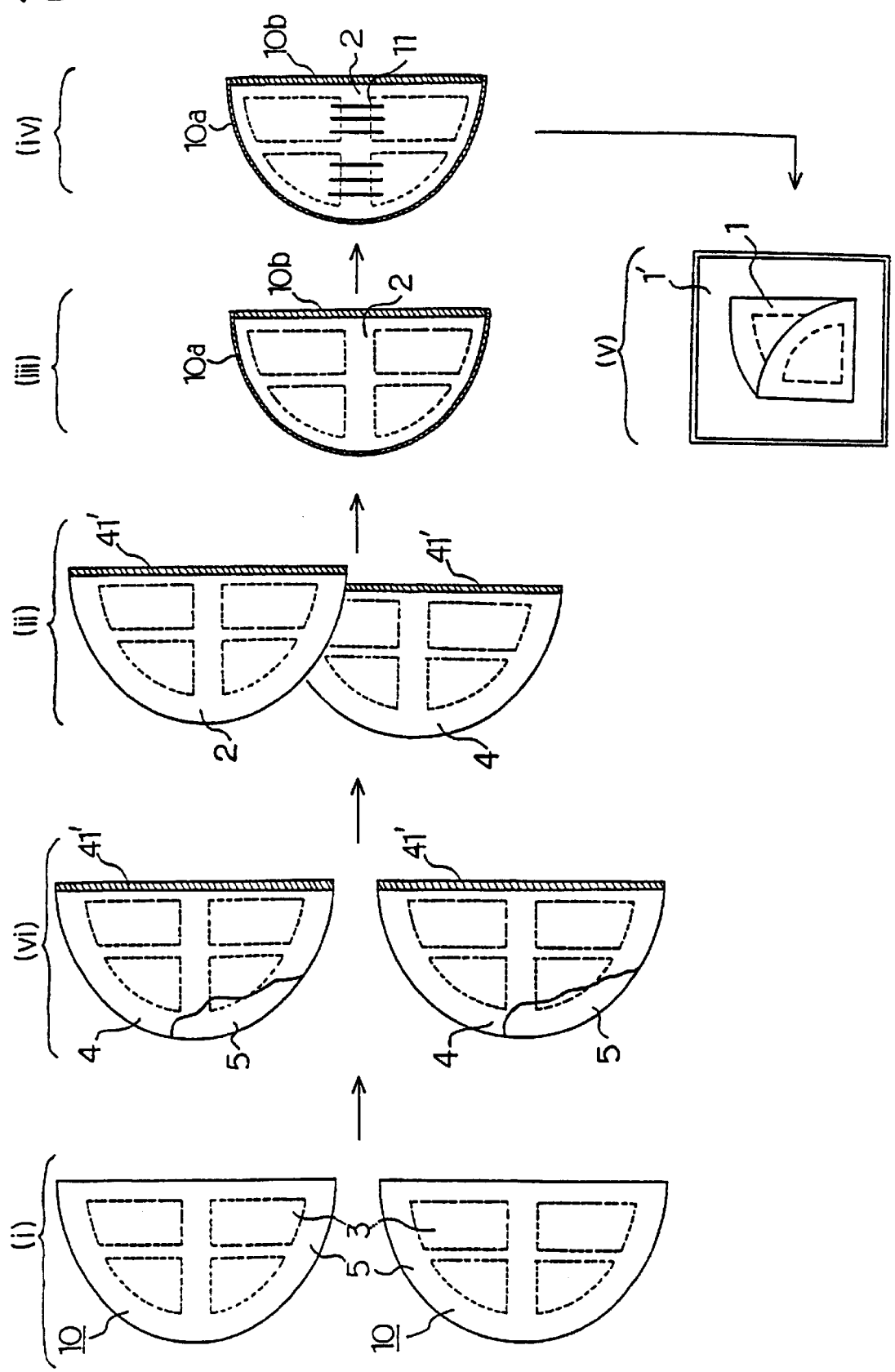
FIG. 7 is a process diagram illustrating an important part of another method for fabricating the heater shown in FIG. 5.

Alternatively, in the fabrication method C, heat-generator-containing sheets 10 of a semi-elliptical shape are produced in the heat-generator-containing sheet producing step (i) in the same manner as that of the fabrication method B, and the heat-generator-containing sheets 10 of a semi-elliptical shape are fixed to the outer layer sheets 4 of a semi-elliptical shape at their linear peripheries 41' in the outer layer sheet fixing step (vi) as shown in FIG. 7.

Next, the overlaying step (ii) is performed by overlaying the heat-generator-containing sheets 10 on each other, to which the outer layer sheets 4 are respectively fixed, in the same manner as that of the overlaying step in the fabrication method B except that the heat-generator-containing sheets are overlaid on each other so that the outer layer sheets 4 are in contact with each other. The sealing step (iii) is performed in the same manner as that of the fabrication method B.

Depending on the necessity, an elastic member attaching step (iv), a packaging step (v), and the like are further performed so as to obtain a heater 1 (a packaged product 1' of the heater 1) of the present embodiment.

In the heater 1 obtained by the fabrication method C, the fixing of the outer layer sheets 4 is performed at curved and linear peripheries 10a and 10b thereof

[As to Fabrication Method D (Not Shown)]

In the fabrication method D, after performing the heat-generator-containing sheet producing step, the overlaying step, and the sealing step in the same manner as that of the fabrication method A or B, cutting along the linear periphery and unsealing are performed so as to form a cap. The obtained cap is reversed so that the air-permeable sheet becomes an outer surface thereof In this manner, the cap 20 as shown in FIG. 1 is produced.

Next, the outer layer cap 40 is put over the obtained cap 20, and the fixing of the caps is performed along the edges thereof at the opening as the above-described predetermined positions so as to obtain the heater of the present embodiment shown in FIG. 5.

A method for fabricating the outer layer cap is not limited to any particular method. Also, the fixing means is not limited to any particular means, and includes methods using heat sealing, an adhesive, or the like.

Next, the third embodiment of the present invention will be described in detail.

Points different from those of the above-described first and second embodiments will be specifically described, and the same points as those of the above-described first and second embodiments will be omitted. Regarding points which will not be specifically described, the description made in the description of the first and second embodiments will be suitably applied thereto.

Figure 8:
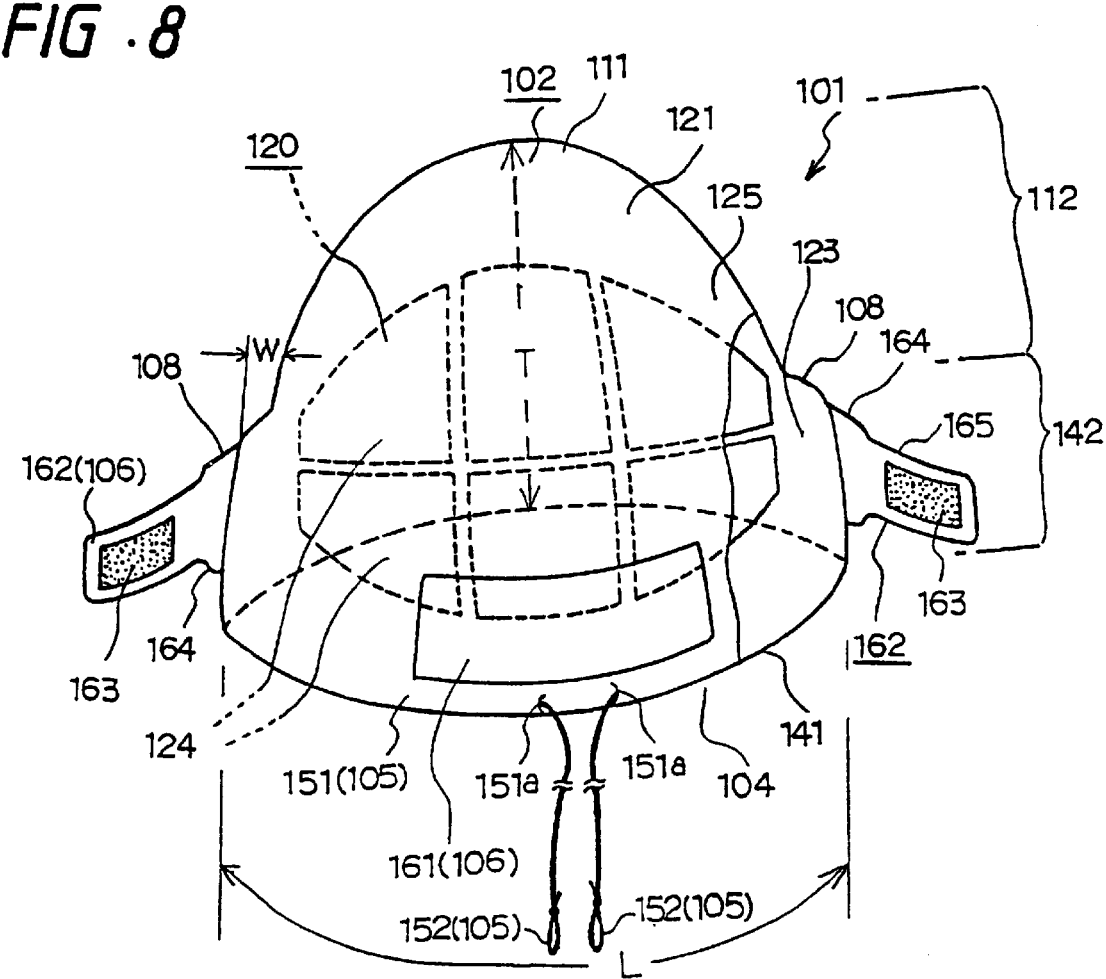
FIG. 8 is a perspective view showing the third embodiment of a heater according to the present invention.

As shown in FIG. 8, a heater 101 of the present embodiment is a heater for heating one's hair and scalp, which comprises a heating cap 102 as a cap having a heating section 120.

In the heater 101 of the present embodiment, the heating section 120 is formed of a plurality of warmers 124, and the heating cap 102 is formed by joining together two heating sheets 121 as heat-generator containing sheets each having the heating section 120. Therefore, the two heating sections 120 are provided on both of the front and rear sides of the heater 101.

The heating sheet 121 and the heating section 120 comprise a waterproof inner layer sheet 123, an air-permeable sheet 125 disposed so as to cover the entire surface of the inner layer sheet 123, and a plurality of warmers 124 formed by beat generators interposed between and held by the inner layer sheet 123 and the air-permeable sheet 125.

In the heating cap 102, peripheries (curved peripheries 122a) of the two heating sheets 121 of generally the same shape are joined and fixed together so that an opening 104 of the cap is formed and the respective inner layer sheets 123 form an inner surface of the cap.

The curved peripheries 122a are joined and fixed together by heat sealing with the air-permeable sheets 125 being in contact with each other. The sealed portion thereof locates at the side of the inner surface of the heating cap 102 (heater 101).

The respective warmers 124 are separated from one another by joining the inner layer sheet 123 and the. air-permeable sheet 125 together.

The heating section 120 includes a plurality of warmers 124 which are arranged in a generally elliptical shape whose end portions at opposite ends in the longitudinal direction are truncated.

In the present embodiment, six warmers 124 are disposed, and thus the heating section 120 which is divided into six portions is formed.

The heating cap 102 of the present embodiment comprises an opening side region 142 located closer to the opening 104, in which a cross sectional area of the heating cap gradually decreases towards a top portion 111, and a top portion side region 112 located closer to the top portion 111, in which a cross sectional area of the heating cap gradually decreases towards the top portion. The opening side region 142 and the top portion side region 112 are divided by a stepped portion 108 where a cross sectional area of the heating cap 102 rapidly decreases. Since the top portion side region 112 has a narrower width and the opening side region 142 has a broader width, the cap can be fitted closely to the head, and ease of wearing can be realized.

In the present embodiment, there is provided opening periphery fitting means 105 for fitting a periphery 141 of the opening 104 closely to the head of a wearer. More specifically, the opening periphery fitting means 105 is provided substantially over the entire region of the periphery 141 of the opening 104. The opening periphery fitting means 105 comprises a tube-like border portion 151 having two edges 151a, and a string member 152 running through the inside of the border portion 151 so that ends thereof extend beyond both of the edges 151a, 151a.

Since the opening periphery fitting means 105 is provided, the periphery 141 of the opening 104 can be fitted closely and thus secured to the head when the heater 101 of the present invention for heating the hair and scalp is worn.

Moreover, in the present embodiment, there is provided opening side region fitting means 106 for fitting the opening side region 142, which is positioned closer to the opening 104, closely to the head of a wearer. More specifically, the opening side region fitting means 106 comprises a female member of a mechanical fastener as an engagement member 161 which is disposed along the periphery of the opening 104, and a fastening member 162 comprising a fastening tape having a male member of the mechanical fastener as a fastening portion 163 to be detachably engaged with the engagement member 161.

The fastening member 162 comprises a fixed portion 164 with a wide width, and an unrestrained portion 165 having a width smaller than that of the fixed portion 164, on which the fastening portion 163 is disposed at the side of the tip thereof The fixed portion 164 is heat-sealed to the heating sheet 120 at the rear side of the cap in FIG. 8 in a direction inclining downwardly so that the unrestrained portion 165 is pointed downwardly. The engagement member 161 has the shape of a rectangle, and is disposed on the heating sheet 120 at the front side of the cap in FIG. 8 so as to be located closer to the opening 104, i.e., at the lower part of the cap. Incidentally the edges 151a, 151a are also positioned below the engagement member 161. The cap is made so that the best ease of wearing is achieved when the cap is worn with both of the engagement member 161 and the edges 151a, 151a being at the front side of the wearer.

A high thermal conduction sheet (not shown) is provided between the plurality of warmers 124. The high thermal conduction sheet is disposed so as to bury the space between the warmers, thereby connecting the warmers 124. As a result, the unevenness of the heating can be further reduced.

As the inner layer sheet 123, a raw material having water resistance and flexibility, e.g., a polyethylene sheet, a polypropylene sheet, a vinyl chloride sheet, etc., is used.

In addition to an air-permeable sheet used, for example, in a general disposable pocket warmer, any air-permeable sheet can be used as the air-permeable sheet 125 without any particular limitations.

In the present embodiment, as in the general disposable pocket warmer, the warmer 124 is a heat generator whose main component is iron powder and which generates heat when in contact with an air.

The heater 101 of the present embodiment is folded in a desired shape, then sealed with an air-impermeable sheet in the same manner as that of a general disposable pocket warmer, and placed on the market, for example. When in use, the sheet is unsealed so as to cease the sealed state. The heater can be put on the head for the heating treatment of the hair and scalp in the same manner as that of a general hair cap except that the cap is worn with the heating section 120 being at the front side of the wearer.

A heat generation temperature and a heat generation time of the heating cap 102 of the present embodiment can be suitably adjusted by the permeability of the air-permeable sheet and the composition of the heat generator composition. For heating the hair and scalp, it is preferred to make an adjustment to produce the temperature characteristics such that the temperature is raised to 35 to 40° C. within ten minutes and a temperature of 40 to 60° C. is lasted for 10 to 120 minutes in the case where the cap is put on the hair wetted by, e.g., water in a room at 25° C.

The heater 101 of the present embodiment is put on the head through the opening 104. Then, the string member is tightened so that the periphery of the opening is fitted closely to the head by the opening periphery fitting means, while the fastening portion of the fastening member is engaged with the engagement member so that the opening side region is fitted closely to the head.

The heater 101 of the present embodiment can safely heat and treat hair and scalp with such a simple handling. Since the heater is closely fitted to the head, the unevenness of the heating is less likely to occur.

Although the heater structured solely by the heating cap was illustrated and described in the third embodiment, a heater comprising an outer layer cap can be also used. The outer layer cap comprising an air-permeable and water-impermeable outer layer sheet is disposed along the outer surface of the air-permeable sheet, and the heating cap and the outer layer cap are fixed together along the edges thereof at the opening, thereby obtaining the outer layer cap. The outer layer sheet used in such a case is an air-permeable and water-impermeable sheet which provides water resistance and a heat retaining property. For example, an air-permeable/water-impermeable sheet, for example, used for a disposable diaper, or the like, may be used. By comprising the water-impermeable outer layer cap, the heater can be used in a place where it may take water, e.g., in a bath.

In the case where the outer layer cap is used and the opening side region fitting means is provided, e.g., in the case where the above-described fastening member and the above-described engagement member are provided, both of them are provided on the outer layer sheet.

It is not necessary to form the heating cap by using two heating sheets. The heating cap may be formed by one heating sheet or three or more of heating sheets, or may be formed by a combination of the heating sheet and a general resin sheet which does not contain a warmer, or the like.

Instead of the above-described string member, the opening periphery fitting means may be formed by an elastic body such as a rubber.

The opening side region fitting means may be formed by replacing, as the fastening member and the engagement member, a male member and a female member of a mechanical fastener with an adhesive tape and a detachment tape, a button and a string-like member, a hook-like member, or the like. The opening side region fitting means may be provided only on one side, instead of providing it as a pair of members on the respective side.

Next, a heater according to the fourth embodiment of the present invention will be described.

In the following description, points different from those in the first to third embodiments will be specifically described.

Regarding points which will not be specifically described, the description made in the above-described first to third embodiments will be suitably applied thereto.

Figure 9:
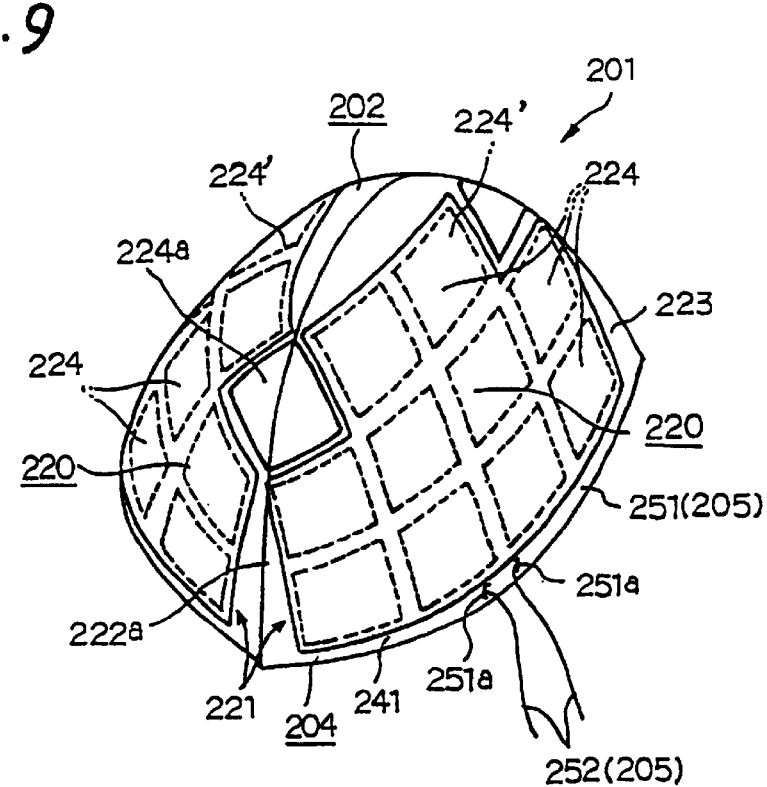
FIG. 9 is a perspective view showing the fourth embodiment of a heater according to the present invention.

As shown in FIG. 9, a heater 201 of the present embodiment as the fourth embodiment of the present invention is a heater for heating hair and scalp which is made up of a heating cap 202 as a cap having a heating section 220.

In the heater 201 of the present embodiment, the heating section 220 is formed by a plurality of rectangular warmers 224, 224a disposed. The two warmers 224a, 224a at the upper corner portions of the heating section 220 extend over two heating sheets 221, 221 with each of which being folded. In the present description, the term "rectangular shape" refers to the concept including a square.

More specifically, the heating sheet 221 comprises a waterproof inner layer sheet 223, and a plurality of warmers 224 provided on one side of the inner layer sheet 223.

Figure 10:
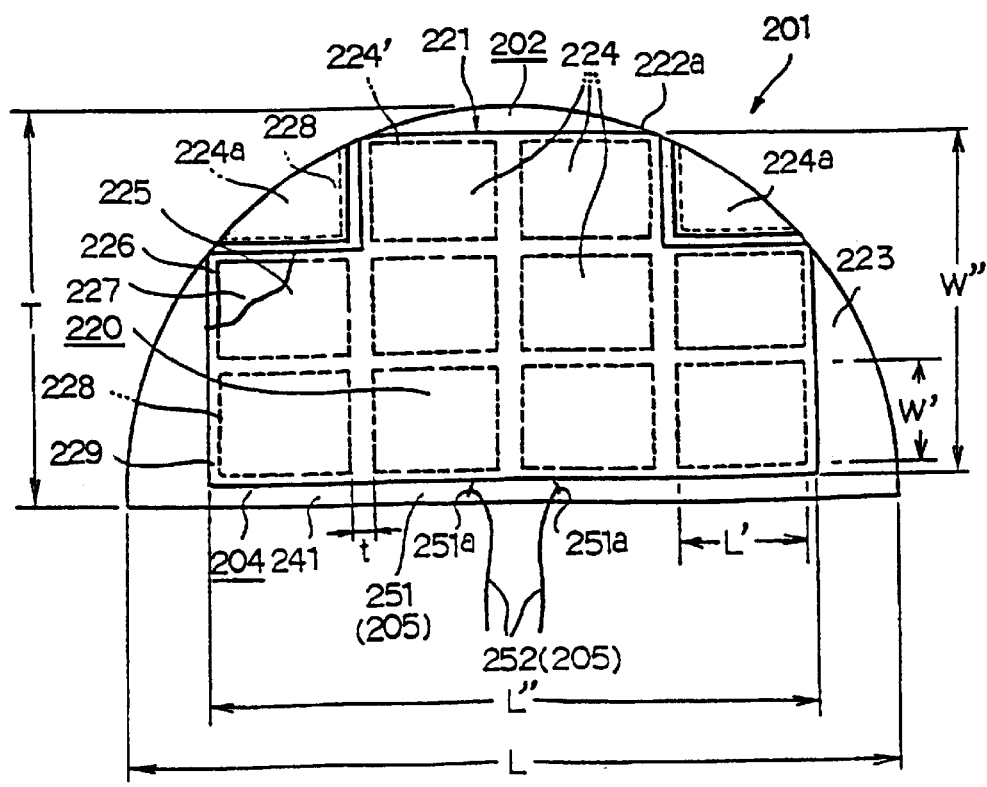
FIG. 10 is a plan view showing a state in which two heating sheets of the heater shown in FIG. 9 are in contact with each other.

As shown in FIG. 10, each of the warmers 224, 224a comprises an adhesive sheet 226 with an adhesive applied to the rear side thereof, an air-permeable sheet 225, and a heat generator 227 interposed between and held by the adhesive sheet and the air-permeable sheet. Each of the adhesive sheet 226 and the air-permeable sheet 225 together forming the warmer 224 has a convex shape. Each warmer 224 is formed by partitioning each of the heat generators 227 disposed in a rectangular shape with a sealing portion 229 formed by sealing the adhesive sheet 226 and the air-permeable sheet 225 so that a storage portion 228 has a rectangular shape. The heat generator 227 is interposed between and held by the air-permeable sheet 225 and the inner layer sheet 223, and the heating section 220 is thus formed. Although the air-permeable sheet 225 covers only a part of the inner layer sheet 223 and does not cover the entire surface thereof, it is sufficient if a part thereof is covered. As long as the heat generator is located between the air-permeable sheet and the inner layer sheet as in the present embodiment, another sheet, e.g., an adhesive sheet, may be interposed between the inner layer sheet and the heat generator, for example.

Regarding the warmer 224a, the heat generator 227 is interposed between and held by the air-permeable sheet 225 and the adhesive sheet 226 of generally the same rectangular shape so that the storage portion 228 has a rectangular shape. The sealing portion 229 is formed along the entire periphery of the warmer 224.

The warmer 224 is fixed to the inner layer sheet 223 via the adhesive of the adhesive sheet 226.

Incidentally the warmer may be formed by mounting the heat generator onto the inner layer sheet, covering the heat generator by the air-permeable sheet, and joining and fixing the air-permeable sheet and the inner layer sheet together at the outer periphery of the heat generator.

The respective warmers 224 are arranged in the respective heating sheets 221 so that the whole shape of each of the heating sections 220 has a shape closer to that of a rectangle. Specifically, in the present embodiment, the heating sections 220 at the respective heating sheets 221 have generally the same shape. In both of the heating sheets 221, the heating section 220 comprises a warmer group 224' and two warmers 224a, 224a positioned at the upper corner portions of the heating section 220. The warmer group 224' includes ten rectangular warmers 224 arranged in a convex shape formed of rows respectively including four, four, and two warmers 224. The warmers 224a, 224a are folded generally along the respective diagonal lines, and extend over both of the heating sheets 221 at the opposite side. Accordingly, the shape of the entire heating section 220 at each of the heating sheets 221 is made to be hexagonal such as that obtained by cutting away the upper corner portions of a rectangle. The heating sections 220 extend over both of the heating sheets 221, 221, and are thus connected with each other.

Since the heating section 220 is formed by the plurality of warmers 224, 224a as described above in the heater 201 of the present embodiment, the cap can be folded with ease. Moreover, since the heating section is formed over the entire region of the heating sheet, a high hair coverage can be realized and the hair and scalp can be heated without the heating unevenness.

Each of the warmers 224 has a rectangular shape, and a preferred size thereof is 4 to 13 cm in length L' and 4 to 9 cm in width W'. One with an area in the range of 15 to 55 $cm^2$ is particularly preferable.

A length L" of the heating section 220 is preferably in the range of 20 to 28 cm, and a width W" is preferably in the range of 15 to 19 cm.

A distance t between the warmers 24 in the heating section 220 is preferably equal to 80 mm or smaller, more preferably, 40 mm or smaller, and most preferably, 20 mm or smaller. By making the distance t equal to or smaller than 80 mm, the heating unevenness does not occur.

Herein, the distance between the warmers 224 refers to the distance between regions (dotted line portions in FIG. 10) whose temperature is raised by the direct heat generation or the like, i.e., the distance between the heat generators 227.

In the present embodiment, as in the general disposable pocket warmer, a heat generator which contains iron powder as its main component and generates heat when in contact with an air is used as a heat generator used in the warmers 224, 224a.

As the air-permeable sheet 225 and the adhesive sheet 226, those used for the general disposable pocket warmer, or the like, can be used.

In the heating cap 202 of the present embodiment, a length L of the half of the periphery of an opening 204 is preferably in the range of 32 to 42 cm, and more preferably in the range of 35 to 39 cm. A depth T of the heating cap 102 is preferably in the range of 15 to 23 cm, and more preferably in the range of 17 to 21 cm.

If the above-described length L is smaller than 32 cm, it is difficult for many people to wear the heating cap. If the above-described length L is greater than 42 cm, a large gap is created between the heating cap and the head, resulting in a poor heating efficiency. Therefore, it is preferred to set the length L within the above-described range.

By setting the above-described depth T to be equal to or greater than 15 cm, it is easy for many people to wear the heater. By setting the above-described depth T to be equal to or smaller than 23 cm, the heating efficiency can be improved without creating a gap between the heater and the head.

Here, the above-described "depth" is a height of the inner surface of the heating cap 202, and refers to a length of a line connecting between the midpoint of the linear opening periphery and the apex of the cap when the cap is folded so that the opening periphery forms a linear line (in the present embodiment, the cap is folded so that the front and rear sides of the cap are in contact with each other and the cap thus forms a semicircular shape).

The moisture permeability of the air-permeable sheet 225 is preferably in the range of 300 to 4000 $gr/m^2 \cdot day$, and more preferably in the range of 500 to 2000 $gr/m^2 \cdot day$.

If the above-described moisture permeability is less than 300 $gr/m^2 \cdot day$, a problem such that the hair wetted by a hair treatment agent is not sufficiently heated is caused. If the moisture permeability is greater than 4000 $gr/m^2 \cdot day$, it is dangerous to use the heater because the temperature of the warmer is raised too high, and the heating section is expanded due to a water vapor generated from the warmer.

The above-described moisture permeability is measured under the condition such that the temperature is 25° C. and the relative humidity is 90% in accordance with the method of JIS Z0208.

As the air-permeable sheet 225 having such a moisture permeability, any air-permeable sheet can be used without any particular limitation as long as it satisfies the above-described moisture permeability. Examples include porous polyethylene film obtained by stretching polyethylene resin, a perforated polyethylene laminated film, and the like. Specifically, the former includes "Pressron" (trade name) manufactured by Nitto Denko and "TSF" (trade name) manufactured by Kohjin, and the latter includes Nippon Matai perforated sheet, and the like.

In the case where the air-permeable sheet having the above-described moisture permeability is used, it is possible to quickly and sufficiently heat the hair even wetted by a hair treatment agent.

The heat generation temperature and heat generation time of the heating cap 202 of the present embodiment are the same as those in the heater of the third embodiment.

The heater of the present invention does not necessarily need to be fabricated by attaching two sheets to each other as long as the final product takes a form such as that obtained by attaching two heating sheets to each other as described above. The heater of the present invention may be formed by attaching three or more sheets to one another.

The heater 201 of the present embodiment is folded in a desired shape, then sealed with an air-impermeable sheet in the same manner as that of a general disposable pocket warmer, and placed on the market, for example. When in use, the sheet is unsealed so as to cease the sealed state. The heater can be put on the head for the heating treatment of the hair and scalp in the same manner as that of a general hair cap except that the heater is worn with the heating section 220 being at the front side of the wearer.

The heater 201 of the present embodiment is formed by disposing the warmers each having a rectangular shape as described above. Since it is easy to fabricate the warmers each having a rectangular shape, the productivity of the heater is high. Also, it is easy to dispose the warmers at the upper corner portions of the heater. By disposing the warmers at the corner portions, it is possible to heat the entire head uniformly, thereby not causing the heating unevenness.

The heater 201 of the present embodiment makes it possible to safely heat and treat the hair and scalp with such a simple handling. Also, since the heating section 220 is provided as described above, the heating unevenness does not occur.

The heater 201 of the present embodiment can be obtained by attaching the warmers obtained by a known method onto the inner layer sheet in a predetermined shape so as to produce the heating sheet on which the heating section in a predetermined shape is formed; by folding the obtained heating sheet into two with the air-permeable sheet side being the inner side, or overlaying the obtained two heating sheets on each other with the air-permeable sheet side being the inner side; sealing the peripheries overlaid on each other, and the like.

Other preferred fabrication methods include a method such that individual warmers 224, 224*a* are fabricated; these warmers are sealed and packaged with an oxygen-impermeable film; the warmers 224, 224*a* which are taken out from the unsealed film are attached to a separately-fabricated cap in which a heating section has not yet formed via an adhesive or by heat sealing so as to fabricate the heating cap 202; and the heating cap 202 is individually packaged with an oxygen-impermeable film.

Incidentally the heater of the fourth embodiment may have an outer layer cap which comprises an air-permeable and water-impermeable outer layer sheet and which is disposed along the outer surface of the air-permeable sheet in the above-described heating cap. In such a heater, the above-described heating cap and the outer layer cap are fixed together along the edges thereof at the opening. The outer layer sheet used in this case is an air-permeable and water-impermeable sheet which produces water resistance and a heat retaining property. For example, an air-permeable/water-impermeable sheet, for example, used for a disposable diaper, or the like, may be used. By comprising the water-impermeable outer layer cap, the heater can be used in a place where it may take water, e.g., in a bath.

In the above-described embodiment, there may be provided opening side region fitting means for fitting the opening side region, which is positioned closer to the opening 204, closely to the head of a wearer. As a specific example of the opening side region fitting means, the opening side region fitting means can be structured by a female member of a mechanical fastener as an engagement member which is disposed along the periphery of the opening 204, and a fastening member comprising a fastening tape having a male member of the mechanical fastener as a fastening portion to be detachably engaged with the engagement member. The fastening member comprises a fixed portion with a wide width, and an unrestrained portion having a width smaller than that of the fixed portion, on which the fastening portion is disposed at the side of the tip thereof The fixed portion is preferably fixed, via an adhesive, to the heating sheet at the rear side of the cap in FIG. 1 in a direction inclining downwardly so that the unrestrained portion is pointed downwardly. The engagement member has the shape of a rectangle, and is preferably disposed on the heating sheet at the front side of the cap in FIG. 9 so as to be located closer to the opening, i.e., at the lower part of the cap.

A high thermal conduction sheet may be provided between the plurality of warmers 224. The high thermal conduction sheet is disposed so as to bury the space between the warmers, thereby connecting the warmers 224. As a result, the heating unevenness can be further reduced.

Although the adhesive sheet is used in the above-described embodiment, an adhesive tape can be used without using the adhesive sheet, or the attachment can be performed via an adhesive.

EXAMPLE

Example 1

By using an air-permeable sheet, an inner layer sheet, and a heat generator described below, the heater shown in FIG. 8 was fabricated in such a manner that the length of the half of the periphery thereof is 37 cm, the height thereof is 21 cm, the distance between the warmers is 2 cm, and the size of the heating section of a generally elliptical shape is 17 cm in height×24 cm in width.

air-permeable sheet; the thickness of 0.2 mm, the moisture permeability of 800 gr/m$^2$·day inner layer sheet; a sheet with the thickness of 0.06 mm whose raw material is polyethylene heat generator; a powder aggregate including iron powder as its main component to which sodium chloride, activated carbon, calcium silicate, vermiculite, and water are added in respective amounts of 1.8, 11.4, 4.8, 10.4, and 31.6 parts by weight with respect to 100 parts by weight of the main component. 10.6 to 10.7 g of the powder aggregate was used for each warmer.

Comparative Example 1

A heater was obtained in the same manner as that of Example 1 except that the moisture permeability of the air-permeable sheet was 280 gr/m²·day.

Comparative Example 2

A heater was obtained in the same manner as that of Example 1 except that the moisture permeability of the air-permeable sheet was 4300 gr/m²·day.

The thus-obtained heaters were used in accordance with the following usage and tested by performing the following tests. The results are shown in Table 1.

Usage; 100 gr of water thickened by 2 gr of xanthan gum was applied to the hairs of five monitors with medium length hair (38 cm); a plurality of thermocouples were arranged in suitable positions in the hair; the heaters were worm the temperature was monitored and feelings of the subjects were recorded; and the following evaluation criteria were evaluated.

Quickness; evaluation was conducted on whether heating can be performed quickly by the following evaluation criteria.

⊚; the average of the thermocouples reached 40° C. within one minutes.

○; the average of the thermocouples reached 40° C. in one to five minutes.

×; it took more than five minutes for the average of the thermocouples to reach 40° C.

Heating performance; evaluated based on whether each monitor felt that the temperature was moderate, did not feel the temperature, or felt that the temperature was too high.

Evenness; if a temperature difference between the thermocouples is within ±5° C., evenness is recognized and indicated by ○.

The expansion of the heating section was checked by visual observation, indicating "Yes" if the expansion was perceived, and indicating "No" if the expansion was not perceived.

TABLE 1

|  | Example 1 | Comparative Example 1 | Comparative Example 2 |
| --- | --- | --- | --- |
| Quickness | ○ | X | ⊚ |
| Heating Performance | Moderate | Not feel the temperature | Too high |
| Evenness | ○ | ○ | ○ |
| Expansion of Heating section | No | No | Yes |

INDUSTRIAL APPLICABILITY

According to the present invention, it is possible to provide a heater which is suitable for use in hair treatments such as hair curling or waving, treatment, hair softening, the straightening of curled hair, resilience rendering, the improvement of a hair condition, and a coloring; and hair treatments such as hair growing and fostering treatments, and a scalp care; which can minimize the loss of iron powder due to the heat generation during the fabrication thereof, whose handling when in use is simple; which has a small temperature variation; and whose fabrication process is simple.

What is claimed is:

1. A heater, comprising a cap having a heating section, wherein said heating section comprises a waterproof inner layer sheet, an air-permeable sheet disposed so as to cover said inner layer sheet, and a plurality of heat generators which are interposed directly between and held by said inner layer sheet and said air-permeable sheet and which generate heat when in contact with air, and wherein said heat generators are arranged substantially over an entire surface of the cap.

2. The heater according to claim 1, further comprising an outer layer cap comprising an air-permeable and water-impermeable outer layer sheet that is disposed along an outer surface of said air-permeable sheet in said cap, wherein said cap and said outer layer cap are fixed together at respective opening sides thereof.

3. The heater according to claim 1, wherein said heating section is formed of a plurality of warmers, and a space between two warmers adjacent to each other is equal to 80 mm or smaller.

4. The heater according to claim 1, further comprising opening fitting means for fitting an opening of said cap closely to a head of a wearer.

5. The heater according to claim 1, further comprising side region fitting means for fitting a side region of said cap closely to a head of a wearer, said side region being adjacent said opening.

6. The heater according to claim 1, wherein a moisture permeability of said air-permeable sheet is in the range of 300 to 4000 gr/m²·day.

7. The heater according to claim 2, wherein said outer layer sheet is water-impermeable and made of a moisture-permeable sheet having a moisture permeability higher than that of said air-permeable sheet, and a moisture permeability of said moisture-permeable sheet is equal to 400 g/m²·day or more.

* * * * *